United States Patent [19]

Palmer et al.

[11] Patent Number: 4,772,624
[45] Date of Patent: Sep. 20, 1988

[54] 1,4-BIS-SUBSTITUTED-2,6,7-TRIOXABICY-CLO(2.2.2)-OCTANES HAVING ETHYNYL SUBSTITUTED PHENYL GROUP

[75] Inventors: Christopher J. Palmer, Ipswich, United Kingdom; John E. Casida, Berkeley, Calif.

[73] Assignee: The Regents of the University of California, Berkeley, Calif.

[21] Appl. No.: 779,167

[22] Filed: Sep. 23, 1985

Related U.S. Application Data

[63] Continuation-in-part of Ser. No. 692,818, Jan. 23, 1985, abandoned, which is a continuation-in-part of Ser. No. 575,843, Jan. 30, 1984, abandoned.

[51] Int. Cl.$^4$ ............... A01N 43/32; C07D 323/04
[52] U.S. Cl. ...................... 514/452; 549/363
[58] Field of Search ................ 514/452; 549/363

[56] References Cited

U.S. PATENT DOCUMENTS 3,113,068 12/1963 Wotiz .................. 514/752
3,686,224 8/1972 Dettner .................. 549/363

FOREIGN PATENT DOCUMENTS 0211598 2/1987 European Pat. Off. ......... 549/363
0059985 7/1981 Japan ..................... 549/363

OTHER PUBLICATIONS

Nishida et al., "Alkyd Resin Adhesives", CA 104 208533 z.

Primary Examiner—Glennon H. Hollrah
Assistant Examiner—A. Owens
Attorney, Agent, or Firm—Fliesler, Dubb, Meyer and Lovejoy

[57] ABSTRACT

A compound of the formula

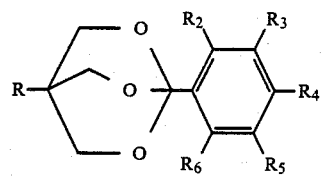

wherein R is $C_3$–$C_{10}$ normal- or branched- alkyl or cycloalkyl, $C_3$–$C_{10}$ normal- or branched- alkyl or cycloalkyl having one or more halogen, cyano, $C_1$–$C_2$ partially or completely halogenated alkyl, or $C_1$–$C_3$ alkoxy or partially or completely halogenated alkoxy substituents, $C_3$–$C_{10}$ cycloalkyl having $C_1$–$C_2$ alkyl substituents, phenyl, or phenyl having one or more halogen, cyano, nitro, ethynl, $C_1$–$C_2$ alkyl or partially or completely halogenated alkyl, or $C_1$–$C_3$ alkoxy or partially or completely halogenated alkoxy substituents; wherein at least one of $R_2$–$R_6$ is ethynyl; and wherein the remainder of $R_2$–$R_6$ are independently either hydrogen, halogen, $C_1$–$C_2$ alkyl, partially or completely halogenated $C_1$–$C_2$ alkyl, $C_1$–$C_3$ alkoxy, partially or completely halogenated $C_1$–$C_3$ alkoxy, ethynyl, nitro, cyano, or azido. Such a compound is useful in killing pests, particularly insects.

8 Claims, No Drawings

1,4-BIS-SUBSTITUTED-2,6,7-TRIOXABICYCLO(2.2.2)-OCTANES HAVING ETHYNYL SUBSTITUTED PHENYL GROUP

ACKNOWLEDGEMENT OF GOVERNMENT SUPPORT

This invention was made with Government Support under Grant No. ES00049 awarded by the National Institutes of Health. The Government has certain rights in this invention.

CROSS-REFERENCE

This application is a continuation-in-part of copending application Ser. No. 692,818 filed Jan. 23, 1985, now abandoned, which is in turn a continuation-in-part of copending application Ser. No. 575,843 filed Jan. 30, 1984 both now abandoned.

TECHNICAL FIELD

The present invention relates to pesticides which are 1,4-bis-substituted-2,6,7-trioxabicyclo-[2.2.2]octanes wherein the 1-position substituent is an ethynyl-substituted phenyl group.

BACKGROUND OF THE INVENTION

Pesticides are chemicals which combat the attacks of various pests on crops, livestock, man and their environment. They include insecticides, fungicides, herbicides (or weed killers), nematicides, molluscicides, acaricides and parasiticides.

Many classes of compounds are known to exhibit pesticidal activity. Unfortunately, known pesticidal compositions may become less effective with time because of the development of resistance in the species against which they are used. Thus, there is a constant need for new types of pesticides.

An ideal pesticide has high effectiveness in controlling pests, and is biodegradable.

The present invention is concerned with providing pesticidal compositions having desirable properties such as those set forth above.

DISCLOSURE OF THE INVENTION

In accordance with an embodiment of the present invention, a compound is set forth having the formula

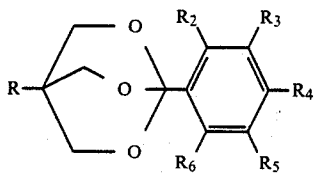

wherein R is $C_3$–$C_{10}$ normal- or branched-alkyl or cycloalkyl, $C_3$–$C_{10}$ normal- or branched-alkyl or cycloalkyl having one or more halogens, cyano, $C_1$–$C_2$ partially or completely halogenated alkyl, or $C_1$–$C_3$ alkoxy or partially or completely halogenated alkoxy substituents, $C_3$–$C_{10}$ cycloalkyl having $C_1$–$C_2$ alkyl substituents, phenyl or phenyl having one or more halogen, cyano, nitro, ethynyl, $C_1$–$C_2$ alkyl or partially or completely halogenated alkyl, or $C_1$–$C_3$ alkoxy or partially or completely halogenated alkoxy substituent; wherein at least one of $R_2$–$R_6$ is ethynyl; and wherein the remainder of $R_2$–$R_6$ are independently either hydrogen, halogen, $C_1$–$C_2$ alkyl, partially or completely halogenated $C_1$–$C_2$ alkyl, $C_1$–$C_3$ alkoxy, partially or completely halogenated $C_1$–$C_3$ alkoxy, ethynyl, nitro, azido or cyano.

In accordance with another embodiment of the present invention a method of killing pests is set forth which comprises contacting the pests with an effective amount for killing the pests of a compound having the above formula.

The preferred pesticidal compositions of the present invention have exceptionally high pesticidal activity, particularly when used with a synergist, and are biodegradable. In particular, they have been shown to exhibit significant pesticidal activity against the common housefly.

BEST MODE FOR CARRYING OUT INVENTION

In accordance with the present invention, a compound is provided having the formula (I) set forth above. It has been shown that this class of compounds includes a number of chemicals which exhibit very high pesticidal activity.

Table 1, which follows, shows the effectiveness for control of houseflies of compounds which fall within the general formula (I), both alone and with the synergist piperonyl butoxide (PB). The abbreviations used in Table 1 are as follows:

Pr—propyl, Bu—butyl, Hex—hexyl, Ph—phenyl, n—normal, t—tertiary, and c—cyclo.

Other abbreviations which appear in later tables are as follows:

Me—methyl, Et—ethyl, Pen—pentyl, Hept—heptyl, i—iso and s—secondary.

TABLE 1

Toxicity to *Musca domestica* both Alone and with the Synergist Piperonyl Butoxide of 1,4-Bis-Substituted-2,6,7-trioxabicyclo[2.2.2]octanes wherein the 1-Substituent is an Ethynyl-Substituted Phenyl Group

| | | $LD_{50}$, μg/g | |
|---|---|---|---|
| 4-Substituent | 1-Substituent | With Synergist (PB) | Alone |
| n-Pr | 4-ethynyl-Ph | 0.043 | 0.75 |
| c-Hex | 4-ethynyl-Ph | 0.030 | 0.53 |
| t-Bu | 4-ethynyl-Ph | 0.017 | 0.19 |

Those pesticides of the formula (I) which have been tested have been found to exhibit a pesticidal activity, as $LD_{50}$ in micrograms of the pesticide per gram of body weight of a selected pest, of no more than about 1. For example, such an activity has been shown as an insecticide against *Musca domestica*. The same pesticides, when used in combination with a synergist, e.g., PB, have been found to exhibit a pesticidal activity, as $LD_{50}$ in micrograms of the pesticide per gram of body weight of a selected pest, of no more than about 0.1. Such an activity has also been shown as an insecticide against *Musca domestica*. Such high pesticidal activity against *Musca domestica* is not essential in as much as the compounds may show sufficient pesticidal activity against other pests as to make them useful against such other pests.

The use of synergists with pesticides is well known and is discussed in detail in the publication "Mixed-Function Oxidase Involvement in the Biochemistry of Insecticide Synergists", J. E. Casida, *J. Agric. Food Chem.*, 18, 753–772 (1970). The compounds of the present invention become even more effective with synergists which function to inhibit microsomal cytochrome P-450 oxidases that detoxify the pesticide thereby allowing a longer period for pesticidal action and consequently higher toxicity. Such synergists include those listed in the above publication plus other synergists which function in the manner stated.

The compositions of the present invention may be used in combination with an inert carrier that serves as a diluent or vehicle for the active pesticides. For example, the toxicant may be dissolved in petroleum hydrocarbons, tetrahydrofuran, acetone, cellosolves or any other suitable inert carrier prior to use. Alternatively, the toxicant may be adsorbed on a solid inert carrier such as talc, clay, finely ground silica or the like.

Contacting of pests with the pesticides of the present invention can be by any effective and convenient method, including any of the various methods of contacting well known in the art and used for delivering prior art pesticides to insects or other pests. For example, the pesticide may be utilized as a spray, an aerosol, dust or granules, or may be impregnated into or coated onto a structure with which the insect or other pests may come into contact, may be mixed with or impregnated into bait, may be incorporated with a substance or structure which slowly releases it in an area normally frequented by the pest or may be incorporated with and/or into other formulations which are directed into contact with the pest or placed where the pest will be likely to contact such formulations. The pesticides may be mixed with an inert carrier to facilitate delivery of the pesticides to the pests.

The toxicity to houseflies is dependent on both the R substituent and the $R_2$–$R_6$ substituents on the phenyl group (the subscripts 2, 3, 4, 5 and 6 correspond to standard numbering of the aromatic ring positions). It has been previously demonstrated, as reported in applications Ser. Nos. 692,818 and 575,843, that differing groups in the 1- and 4-position of the 1,4-bis-substituted-2,6,7-trioxabicyclo[2.2.2]octanes (of the formula (II): R—C(CH$_2$O)$_3$C—X) lead to different pesticidal activities. Tables 2-5, with the values in Tables 3-5 representing more refined evaluations than those in Table 2, illustrate the dependence of pesticidal activity on the 1- and 4-substituents of such 1,4-bis-substituted compounds.

TABLE 2

Housefly Control by 1,4-bis-Substituted-
2,6,7-trioxabicyclo[2.2.2]octanes Alone
and With the Synergist Piperonyl Butoxide

| R—C(CH$_2$O)$_3$C—X | | Compound | LD$_{50}$, µg/g | |
|---|---|---|---|---|
| R | X | number | With Synergist | Alone |
| t-Bu | 4-BrPh | 25 | 0.4 | 4 |
| c-Hex | 4-ClPh | 8 | 0.4 | 37 |
| t-Bu | 3,4-Cl$_2$Ph | 38 | 1 | 5 |
| c-Hex | c-Hex | 13 | 1 | 13 |

TABLE 2-continued

Housefly Control by 1,4-bis-Substituted-
2,6,7-trioxabicyclo[2.2.2]octanes Alone
and With the Synergist Piperonyl Butoxide

| R—C(CH$_2$O)$_3$C—X | | Compound | LD$_{50}$, µg/g | |
|---|---|---|---|---|
| R | X | number | With Synergist | Alone |
| t-Bu | 4-ClPh | 6 | 1 | 15 |
| n-Pr | 4-ClPh | 2 | 2 | 10 |
| t-Bu | c-Hex | 60 | 2 | 40 |
| c-Hex | 4-FPh | 24 | 2 | >500 |
| t-Bu | 4-FPh | 23 | 3 | >500 |
| t-Bu | 3-ClPh | 21 | 4 | 125 |
| n-Bu | 4-ClPh | 4 | 4 | 23 |
| Ph | c-Hex | 14 | 5 | 225 |
| c-Hex | Ph | 18 | 5 | >500 |
| Ph | 4-ClPh | 9 | 7 | 400* |
| i-Pr | c-Hex | 59 | 8 | >500 |
| i-Pr | 4-ClPh | 3 | 12 | 100 |
| t-Bu | Ph | 17 | 23 | >500 |
| t-Bu | 2-FPh | 19 | 25 | >500 |
| t-Bu | n-Bu | 51 | 50 | 450 |
| n-Pr | Ph | 15 | 60 | >500 |
| n-Pr | n-Bu | 69 | 100 | >500 |
| t-Bu | Ethynyl | 65 | 125 | 150 |
| t-Bu | Benzyl | 68 | 125 | >500 |
| i-Pr | Ethynyl | 64 | 125 | >500 |
| Et | c-Hex | 12 | 225 | >500 |
| Ph | 4-FPh | 45 | 225 | >500 |
| Ph | Ph | 44 | 250 | >500 |
| t-Bu | n-Pr | 49 | 375 | >500 |
| 4-MePh | 4-ClPh | 10 | >150 | >150 |
| t-Bu | H | 46 | >500 | >500 |
| t-Bu | Me | 47 | >500 | >500 |
| t-Bu | Et | 48 | >500 | >500 |
| t-Bu | i-Pr | 50 | >500 | >500 |
| t-Bu | 4-t-BuPh | 37 | >500 | >500 |
| i-Pr | Vinyl | 63 | >500 | >500 |
| i-Pr | 3-PhOPh | 22 | >500 | >500 |
| i-Pr | 1-BrEt | 66 | >500 | >500 |
| i-Pr | 1,2-Br$_2$Et | 67 | >500 | >500 |
| NO$_2$ | 4-ClPh | 11 | >500 | >500 |

*Value based on suspension in acetone with only partial solution.

TABLE 3

Effect of R-Substituent on the Topical
Toxicity to Houseflies of 1-(4-Chlorophenyl)-2,6,7-
trioxabicyclo[2.2.2]octanes and Three 1-Cyclohexyl Analogs

| R-substituent | compound number | LD$_{50}$, µg/g, with PB (and alone) |
|---|---|---|
| Et[a] | 1 | 105 (>500) |
| n-Pr | 2 | 2.5 (23) |
| i-Pr | 3 | 8.3 (140) |
| n-Bu | 4 | 3.5 (17) |
| s-Bu | 5 | 2.7 (58) |
| t-Bu | 6 | 1.5 (10) |
| c-Pen | 7 | 2.0 (21) |
| c-Hex[a] | 8 | 0.53 (10) |
| Ph[a] | 9 | 2.5 (41) |
| 4-MePh | 10 | >500 (>500) |
| NO$_2$ | 11 | >500 (>500) |

[a]Compound numbers and LD$_{50}$ values [µg/g with PB (and alone)] in the 1-c-Hex series are: (12) 4-Et 350 (>500); (13) 4-c-Hex 0.63 (8.5); (14) 4-Ph 7.0 (375).

TABLE 4

Effect of Substitution on 1-Phenyl Group (X) on the Topical Toxicity to Houseflies of
4-Alkyl-2,6,7-trioxabicyclo[2.2.2]octanes and Two 4-Phenyl Analogs

| substituent on 1-phenyl group (X) | compound number | | | | LD$_{50}$, µg/g, with PB (and alone) | | | |
|---|---|---|---|---|---|---|---|---|
| | 4-n-Pr | 4-i-Pr | 4-t-Bu | 4-c-Hex | 4-n-Pr | 4-i-Pr | 4-t-Bu | 4-c-Hex |
| H[a] | 15 | 16 | 17 | 18 | 90 (>500) | 90 (>500) | 23 (>500) | 13 (>500) |
| 2-F | | | 19 | | | | 30 (>500) | |
| 2-Cl | | | 20 | | | | 105 (>500) | |
| 3-Cl | | | 21 | | | | 6.3 (375) | |
| 3-PhO | | 22 | | | | >500 (>500) | | |
| 4-F[a] | | | 23 | 24 | | | 5.5 (>500) | 1.9 (>500) |
| 4-Cl | 2 | 3 | 6 | 8 | 2.5 (23) | 8.3 (140) | 1.5 (10) | 0.53 (10) |

TABLE 4-continued

Effect of Substitution on 1-Phenyl Group (X) on the Topical Toxicity to Houseflies of 4-Alkyl-2,6,7-trioxabicyclo[2.2.2]octanes and Two 4-Phenyl Analogs

| substituent on 1-phenyl group (X) | compound number | | | | $LD_{50}$, μg/g, with PB (and alone) | | | |
|---|---|---|---|---|---|---|---|---|
| | 4-n-Pr | 4-i-Pr | 4-t-Bu | 4-c-Hex | 4-n-Pr | 4-i-Pr | 4-t-Bu | 4-c-Hex |
| 4-Br | | | 25 | 26 | | | 0.83 (3.5) | 0.25 (6.5) |
| 4-CF₃ | | | 27 | | | | 53 (>500) | |
| 4-NO₂ | | 28 | 29 | | | 11 (>500) | 5.0 (>500) | |
| 4-CN | | | 30 | 31 | | | 0.23 (4.8) | 0.65 (115) |
| 4-N₃ | | | 32 | | | | 13 (160) | |
| 4-MeSO₂ | 33 | | | | >500 (>500) | | | |
| 4-MeS | 34 | | | | >500 (>500) | | | |
| 4-MeO | | 35 | | | | 265 (>500) | | |
| 4-Me | | 36 | | | | 250 (>500) | | |
| 4-t-Bu | | | 37 | | | | >500 (>500) | |
| 3,4-Cl₂ | | | 38 | 39 | | | 0.88 (4.3) | 2.5 (30) |
| 3-NO₂,4-Cl | 40 | | | | >500 (>500) | | | |
| 3,4-OCH₂O | 41 | | | | >500 (>500) | | | |
| 2,3,4,5,6-F₅ | | 42 | 43 | | | 135 (>500) | 18 (240) | |

$^a$Compound numbers and $LD_{50}$ values [μg/g, with PB (and alone)] in the 4-Ph series are (44) H 325 (>500) and (45) 4-F 250 (>500).

TABLE 5

Effect of 1-Substituent (X) on the Topical Toxicity to Houseflies of 4-Isopropyl- and 4-t-Butyl-2,6,7-trioxabicyclo[2.2.2]-octanes and Five 4-n-Propyl and two 4-Cyclohexyl Analogs

| 1-substit- | compound no. | | $LD_{50}$, μg/g, with PB (and alone) | |
|---|---|---|---|---|
| uent (X) | 4-i-Pr | 4-t-Bu | 4-i-Pr | 4-t-Bu |
| H | | 46 | | >500 (>500) |
| Me | | 47 | | >500 (>500) |
| Et | | 48 | | >500 (>500) |
| n-Pr | | 49 | | 425 (>500) |
| i-Pr | | 50 | | >500 (>500) |
| n-Bu$^a$ | | 51 | | 55 (450) |
| s-Bu | 52 | | >500 (>500) | |
| n-Pen | | 53 | | 33 (365) |
| neo-Pen | 54 | | >500 (>500) | |
| n-Hex | 55 | | 160 (>500) | |
| c-Pr | 56 | | >500 (>500) | |
| c-Bu | 57 | | >500 (>500) | |
| c-Pen | 58 | | 500 (>500) | |
| c-Hex$^a$ | 59 | 60 | 14 (>500) | 3.5 (165) |
| c-Hept$^a$ | 61 | 62 | 8.5 (300) | 2.0 (44) |
| Vinyl | 63 | | >500 (>500) | |
| Ethynyl | 64 | 65 | 325 (>500) | 90 (175) |
| 1-BrEt | 66 | | >500 (>500) | |
| 1,2-Br₂Et | 67 | | >500 (>500) | |
| Benzyl | | 68 | | 210 (>500) |

$^a$Compound numbers and $LD_{50}$ values [μg/g with PB (and alone)] are: in the 4-n-Pr series (69) 1-n-Bu 155 (>500), (70) 1-(1-bicyclo[2.2.1]heptyl) 125 (>500), (71) 1-(2-bicyclo[2.2.1]heptyl) 10 (160), (72) 1-(cyclohex-3-enyl) 19 (110) and (73) 1-(5-bromo-2-furyl) 68 (500); in the 4-c-Hex series (13) 1-c-Hex 0.63 (8.5) and (74) 1-c-Hept 2.0 (13).

TABLE 6

Toxicity to American Cockroaches of Topically-Applied 1,4-bis-Substituted-2,6,7-trioxabicyclo[2.2.2]octanes

| R—C(CH₂O)₃C—X | | compound | |
|---|---|---|---|
| R | X | number | $LD_{50}$ μg/g, with PB |
| n-Pr | 4-ClPh | 2 | 2 |
| n-Bu | 4-ClPh | 4 | 3 |
| t-Bu | 4-ClPh | 6 | 1$^a$ |
| c-Pen | 4-ClPh | 7 | 2 |
| c-Hex | 4-ClPh | 8 | 1$^a$ |
| Ph | 4-ClPh | 9 | 7 |
| c-Hex | c-Hex | 13 | >8 |
| t-Bu | 4-BrPh | 25 | 1$^a$ |
| c-Hex | 4-BrPh | 26 | 1 |
| t-Bu | 3,4-Cl₂Ph | 38 | >10 |
| t-Bu | c-Hex | 60 | 2$^a$ |

$^a$At least 20-fold synergism by PB.

The data in Tables 2–5 indicate that compounds of the formula R—C(CH₂O)₃C—X are often effective pesticides. R or X may be alkyl, alkenyl, alkynyl, cycloalkyl or cycloalkenyl, each of which may be normal, branched or substituted, or may be aryl or substituted aryl or heterocycle. When R is a normal or branched alkyl, or cycloalkyl or aryl, useful compounds result. Preferably, the number of carbon atoms in R is three to ten. More preferably R is n-propyl, t-butyl, cyclohexyl, cyclopentyl, i-propyl, n-butyl, s-butyl or phenyl. X is preferably cycloalkyl or substituted cycloalkyl or cycloalkenyl having six to ten carbon atoms, normal alkyl, alkynyl, substituted alkyl or substituted alkynyl, or substituted phenyl. Effective pesticides result with cyclohexyl and cycloheptyl substituents. Other useful substituents include n-pentyl, cyclohex-3-enyl and 2-bicyclo[2.2.1]heptyl. The substituents on the phenyl group, when the phenyl group is the group X, are preferably halogens, cyano, nitro or azido groups.

The effect of the R-substituent on the effectiveness of the toxicants both alone and along with PB on houseflies is presented in Table 3.

The effect of substitution on the 1-phenyl group on the topical toxicity to houseflies of 4-alkyl-2,6,7-trioxabicyclo[2.2.2]octanes and of two 4-phenyl analogs was tested. Table 4 presents the results of the testing.

The effect of the 1-substituent on the topical toxicity to houseflies of 4-isopropyl- and of 4-t-butyl-2,6,7-trioxabicyclo[2.2.2]octanes and of five 4-n-propyl and two 4-cyclohexyl analogs was also tested. Table 5 presents the results of the testing.

Tables 2–5 illustrate the fact that the effectiveness of compounds of the general formula (II) R—C(CH₂O)₃-C—X, wherein R and X represent organic substituents, is dependent on the nature of both the R and the X component. Table 6, which follows, shows the toxicity to American cockroaches of various topically-applied 1,4-bis-substituted-2,6,7-trioxabicyclo[2.2.2]octanes.

The data in Table 1 illustrate the very high pesticidal effectiveness of compounds of formula (I) in accordance with the present invention. It is apparent from the data in Tables 1–6 that R (in formula (I)) may be alkyl, alkenyl, alkynyl, cycloalkyl or cycloalkenyl, each of which may be normal, branched or substituted, or may be aryl or substituted aryl or heterocycle. When R is a normal or branched alkyl, or cycloalkyl or aryl, particularly useful compounds result. Preferably, the number of carbon atoms in R, when R is normal- or branched-alkyl or cycloalkyl, is 3 to 10. The $C_3$–$C_{10}$ normal- or branched-alkyl or cycloalkyl groups may have one or more halogens, cyano, $C_1$–$C_2$ partially or completely halogenated alkyl or $C_1$–$C_3$ alkoxy or partially or completely halogenated alkoxy substituents. The $C_3$–$C_{10}$ cycloalkyl may have $C_1$–$C_2$ alkyl substituents. When R is aryl, it may be phenyl or phenyl having one or more halogen, cyano, ethynyl, nitro, azido, $C_1$–$C_2$ alkyl or partially or completely halogenated alkyl, or $C_1$–$C_3$ alkoxy or partially or completely halogenated alkoxy substituents.

It is essential to the practice of the present invention that at least one of $R_2$–$R_6$ be ethynyl. The remainder of $R_2$–$R_6$ are independently either hydrogen, halogen, $C_1$–$C_2$ alkyl, partially or completely halogenated $C_1$–$C_2$ alkyl, $C_1$–$C_3$ alkoxy, partially or completely halogenated $C_1$–$C_3$ alkoxy, ethynyl, nitro, azido or cyano. Preferably, at least one of $R_3$, $R_4$ and $R_5$ is ethynyl and the remainder of $R_2$–$R_6$ are hydrogen, fluorine, chlorine, bromine, cyano, $CF_3$, ethynyl, methyl, ethyl, methoxy, ethoxy, nitro or azido. Pesticidal activity has been demonstrated when one of $R_3$, $R_4$ and $R_5$ is hydrogen. Such activity has also been shown when at least two of $R_3$, $R_4$ and $R_5$ are hydrogen. Particularly effective compounds have been formulated wherein $R_3$ and $R_5$ are hydrogen and $R_4$ is ethynyl.

In accordance with an embodiment of the present invention pests may be killed by a method comprising contacting the pests, with an effective amount for killing them, of a compound with formula (I) wherein R and $R_2$–$R_6$ are as set forth above for formula (I). Pesticidal activity is enhanced through use of a synergist.

Procedures of Synthesis

Methods for making compounds of the formula R—C(CH$_2$O)$_3$C—X (II) can be found in the following publications. "Structure-Toxicity Relationships of 1-Substituted-4-alkyl-2,6,7-trioxabicyclo[2.2.2]octanes," D. S. Milbrath, J. L. Engel, J. G. Verkade and J. E. Casida, *Toxicology and Applied Pharmacology*, 47, 287–293 (1979); "Structure-Toxicity Relationships of 2,6,7-Trioxabicyclo[2.2.2]octanes and Related Compounds," J. E. Casida, M. Eto, A. D. Moscioni, J. L. Engel, D. S. Milbrath and J. G. Verkade, "Toxicology and Applied Pharmacology, 36, 261–279 (1976); "Nuclear Magnetic Resonance in Polycyclic Compounds. II. Long-Range H$^1$-H$^1$ and H$^1$-P$^{31}$ Coupling in Some Adamantane and Bicyclo[2.2.2]octane Derivatives," E. J. Boros, K. J. Coskran, R. W. King and J. G. Verkade, *JACS*, 88, 1140–1143 (1966); "Unusual Behavior of Hexafluorobenzene and Benzene in the Aromatic Nuclear Magnetic Resonance Shift Effect," R. D. Bertrand, R. D. Compton and J. G. Verkade, *JACS*, 92, 2702–2709 (1970); "A New General Synthetic Route to Bridged Carboxylic Ortho Esters," E. J. Corey and N. Raju, *Tetrahedron Letters*, 24, 5571–5574 (1983); and "Bicyclo Ortho Esters by Direct Esterification," R. A. Barnes, G. Doyle, and J. A. Hoffman, *J. Org. Chem.*, 27, 90–93 (1962).

Intermediates for these reactions are described by "Ketene Acetals. XXXIV. Tetra- and Pentamethylene Ketene Acetals," S. M. McElvain and R. E. Starn, Jr., *JACS*, 77, 4571–4577 (1955); "Preparation of Trimethylolisobutane by Condensation of Isovaleraldehyde with Formaldehyde," M. M. Ketslakh, D. M. Rudkovskii, and F. A. Eppel, *Oksosintez, Poluchenie Metodom Oksosinteza Al'degidov, Spritov i Vtorichnykh Produktov na ikh Osnove, Vses. Nauchn.-Issled., Inst. Neftekhim Protsessov* (1963), 156–163; "Extensions of Tollens Condensation," O. C. Dermer and P. W. Solomon, *JACS*, 76, 1697–1699 (1954); and "Cyclic Ethers Made by Pyrolysis of Carbonate Esters", D. B. Pattison, *JACS*, 79, 3455–3456 (1957).

Three specific methods (A–C) have been used to prepare trioxabicyclooctanes. Each procedure started from a triol synthesized from the corresponding substituted-acetaldehyde by hydroxymethylation and subsequent crossed-Cannizzaro reaction (Dermer and Solomon, 1954; Ketslakh et al., 1963). The reaction scheme was:

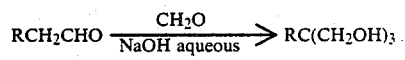

Each trioxabicyclooctane gave appropriate proton nuclear magnetic resonance and mass spectrometry (MS) characteristics.

Procedure A

*Acid*-catalyzed Condensation of a Triol with an Orthocarboxylate (Boros et al., 1966; Bertrand et al., 1970). The equation for the reaction being:

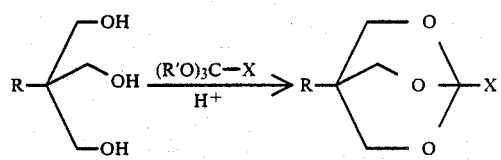

where R' may be alkyl or aryl, preferably methyl or ethyl. For example, a mixture of 2-t-butyl-2-hydroxymethyl-1,3-propanediol (R=t—Bu) (0.4 g, 2.5 mmol), trimethyl orthocyclohexanecarboxylate (X=c—Hex; R'=CH$_3$), (0.5 g, 2.5 mmol) and 4-toluenesulphonic acid (10 mg) was heated to 160° C. until methanol distilled over. The residue was vacuum dried (at 1 mm Hg) and then passed down a short basic alumina column to give trioxabicyclooctane 60 (X=c—Hex; R=t—Bu) (0.6 g, 95%). Directly analogous procedures were used to prepare compounds 1–19, 21–27, 37–39, 44–51, 59 and 63–69.

Intermediate trimethyl orthocarboxylates were commercially available or were synthesized by either of two procedures illustrated with the methyl esters. In the first procedure, the appropriate benzotrichloride or benzotribromide (from bromination of the corresponding toluene with N-bromosuccinimide (NBS)) was subjected to halide displacement with methoxide (McElvain and Venerable, 1950). These methods were as follows:

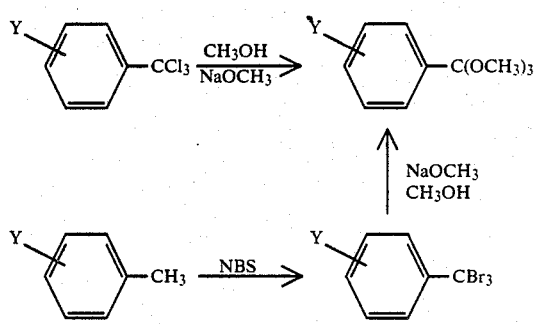

wherein Y represents hydrogen or one or more other groups such as halo or trifluoromethyl.

In the second procedure, the appropriate nitrile was treated with methanol and hydrochloric acid to obtain the imino ester hydrochloride and ultimately the trimethyl orthocarboxylate (McElvain and Starn, 1955). This procedure was as follows:

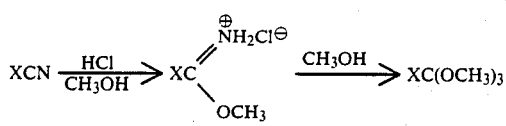

Procedure B

*Rearrangement of an Acylated Hydroxymethyloxetane* (Corey and Raju, 1983). Acylation of 3-substituted-3-hydroxymethyloxetanes (prepared from the appropriate triol via pyrolysis of the carbonate ester) (Pattison, 1957) gives the corresponding oxetane esters which can be rearranged in the presence of boron trifluoride etherate to form trioxabicyclooctanes. The equation for the reaction being:

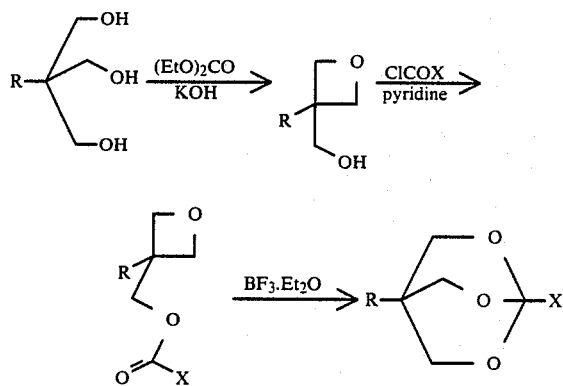

For example, 4-nitrobenzoyl chloride (2.28 g, 12.3 mmol) in dry dichloromethane (4 ml) was added to 3-isopropyl-3-hydroxymethyloxetane (1.6 g, 12.3 mmol) in dry dichloromethane (15 ml) and dry pyridine (2 ml) at 0° C. under a nitrogen atmosphere. The solution was stirred overnight, then extracted with water, dried (sodium sulfate), filtered and evaporated to leave the 4-nitrobenzoyl ester (3.4 g, 99%) as a residue which was not purified further. $^1$H NMR (CDCl$_3$), $\delta$ 1.0 [6H, d, (CH$_3$)$_2$C], 2.3 [1H, m, C-CH], 4.55 [2H, s, CH$_2$OCO], 4.6 [4H, d of d, CH$_2$OCH$_2$], 8.3 [4H, q, aromatic]. This residue was dissolved in dry dichloromethane (15 ml) under a nitrogen atmosphere, cooled to $-55°$ C. and boron trifluoride etherate (2 ml) was added. The mixture was allowed to warm to room temperature and was then quenched with triethylamine, evaporated to dryness and partitioned between dichloromethane and water. The organic layer was separated, dried (potassium carbonate) and evaporated. The residue was purified by passage through a short basic alumina column to afford trioxabicyclooctane 28 (X=4—NO$_2$Ph; R=i—Pr) (1.7 g, 50%). Directly analogous procedures were used to prepare compounds 16, 20, 29–36, 40–43, 53–58, 61, 62 and 70–74.

Procedure C

*Acid-catalyzed Condensation of a Triol Directly with a Carboxylic Acid, Acid Chloride, or the like* (Barnes et al., 1962). The equation for the reaction being:

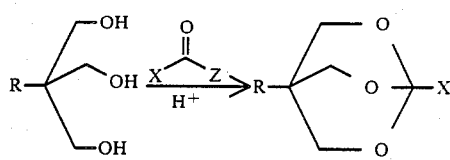

wherein Z represents hydroxyl, halo, acyl, cyano, or other group which it is suitable and customary to use in condensation reactions. Thus, a solution of 2-isopropyl-2-hydroxymethyl-1,3-propanediol (3 g, 20 mmol), 2-methylbutyric acid (2 g, 20 mmol) and 4-toluenesulphonic acid (20 mg) in benzene (100 ml) was heated to reflux for 12 hours and the water formed was separated off. The solution was evaporated down to low volume and then distilled under reduced pressure to give trioxabicyclooctane 52 (X=s—Bu; R=i—Pr) (2.55 g, 62%).

The 4-substituted-1-(4-ethynylphenyl)-2,6,7-trioxabicyclo[2.2.2]octanes of formula (I) were prepared via Procedure B above. Acylation of 3-substituted-3-hydroxymethyloxetanes with 4-(1,2-dibromoethyl)-benzoyl chloride gave the corresponding oxetane esters which were rearranged in the presence of boron trifluoride etherate to form the 4-substituted-1-(4-[1,2-bromoethyl]phenyl)-2,6,7-trioxabicyclo[2.2.2]octanes. These in turn were dehydrobrominated using sodamide in liquid ammonia to give the 4-substituted-1-(4-ethynylphenyl)-2,6,7-trioxabicyclo[2.2.2]octanes. Equations for the reactions are:

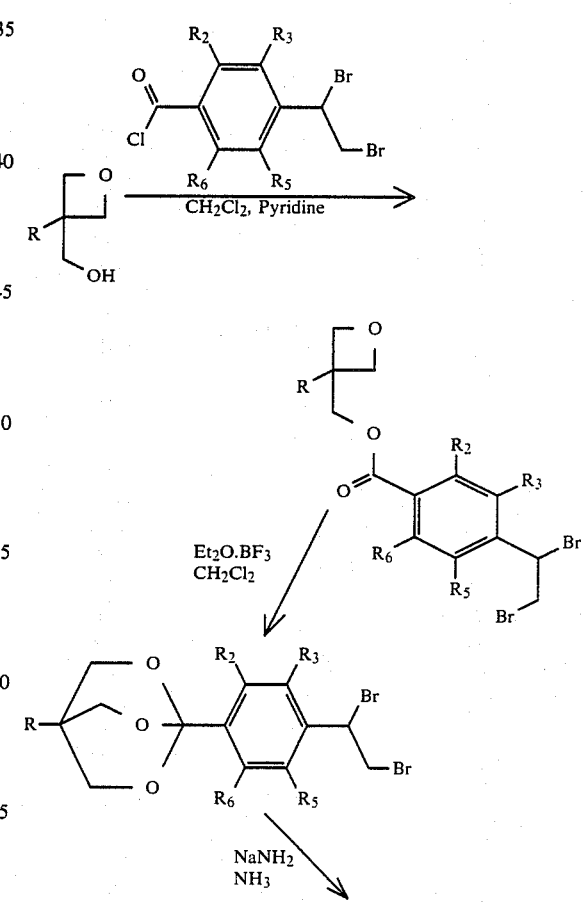

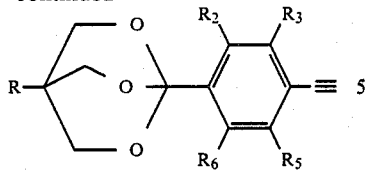

The synthesis procedure for compounds in accordance with the present invention will be better understood by reference to the following illustrative procedures.

Procedure 1

Preparation of 4-(1,2-dibromoethyl)benzoyl chloride

To a solution of p-vinylbenzoic acid (5 g, 34 mmol) in chloroform (50 ml) at 0° C. was added $Br_2$ (35 mmol) in chloroform with stirring. The mixture was allowed to stand overnight and then was evaporated to dryness, leaving crude 4-(1,2-dibromoethyl)benzoic acid, 10.4 g (99%). This was suspended in dry benzene (100 ml), thionyl chloride (8.3 g) was added and the mixture was heated sufficiently to cause it to reflux for 3 hours. The solution was evaporated to dryness to give the acid chloride as a solid.

Procedure 2

Preparation of 4-t-butyl-1-(4-ethynylphenyl)-2,6,7-trioxabicyclo[2.2.2]octane

To a stirred solution of 3-t-butyl-3-hydroxymethyloxetane (2.16 g, 15 mmol) in dry dichloromethane (30 ml) containing pyridine (1.5 ml) at 0° C. under a nitrogen atmosphere was added a solution of 4-(1,2-dibromoethyl)benzoyl chloride (5 g, 16 mmol) which was produced in accordance with Procedure 1. The mixture was allowed to warm to room temperature and was stirred overnight. The resulting solution was washed with water, dried over sodium sulfate and evaporated to leave the oxetane ester, 6.5 g. The product was characterized by NMR (300 MHz, $CDCl_3$) δ 1.05 (9H, s, $(CH_3)_3C$), 3.95–4.1 (2H, m, $CH_2Br$), 4.45 (2H, s, $CH_2$—O), 4.6 (4H, d of d, $CH_2$—O—$CH_2$), 5.15 (1H, d of d, Ar—CHBr), 7.5 (2H, d, aromatic), 8.1 (2H, d, aromatic).

To a stirred solution of the oxetane ester (6.5 g, 15 mmol) in dry dichloromethane (35 ml) under a nitrogen atmosphere at −70° C. was added boron trifluoride etherate (1 ml). The solution was allowed to warm to room temperature and was stirred overnight. The reaction mixture was quenched with dry triethylamine and evaporated to dryness. The residue was partitioned between water and dichloromethane and the organic layer was separated, dried over $K_2CO_3$ and evaporated to leave crude 4-t-butyl-1-(4-(1,2-dibromoethyl)phenyl)-2,6,7-trioxabicyclo[2.2.2]octane. This compound was characterized by NMR (300 MHz, $CDCl_3$), δ 0.9 (9H, s, $(CH_3)_3C$), 3.9–4.05 (2H, m, $CH_2Br$), 4.15 (6H, s, $(CH_2O)_3$), 5.1 (1H, d of d, ArCHBr), 7.35 (2H, d, aromatic), 7.6 (2H, d, aromatic).

Small pieces of sodium were added to liquid ammonia until a blue color persisted. Ferric nitrate (100 mg) was added and the solution was stirred. When the solution turned colorless, sodium (6 g) was added in small pieces. After about 30 to 35 minutes following the addition the blue color disappeared and a solution of the above dibromoethylphenyl bicyclooctane in tetrahydrofuran was added to the solution. The ammonia was allowed to evaporate overnight and the residue was partitioned between ether and ice/water. The organic layer was separated, dried over $K_2CO_3$ and evaporated to leave crude 1-(4-ethynylphenyl)bicyclooctane. This was purified by chromatography on alumina (made basic with $NH_3$) and elution with dichloromethanehexane (1:4) and recrystallization from hexanedichloromethane. The compound was characterized by NMR (300 MHz, $CDCl_3$): δ 0.9 (9H, s, $(CH_3)_3C$), 3.05 (1H, s, C≡CH), 4.15 (6H, s, $(CH_2O)_3$), 7.45 (2H, d, aromatic), 7.55 (2H, d, aromatic). The compound was also characterized by mass spectrometry ($M^+272$) and was found to have a melting point of 167°–168 C.

Procedure 3

Preparation of 4-cyclohexyl-1-(4-ethynylphenyl)-2,6,7-trioxabicyclo[2.2.2]octane Utilizing Procedure 2, 4-cyclohexyl-1-(4-ethynylphenyl)-2,6,7-trioxabicyclo[2.2.2]octane was prepared from its respective oxetane. The 3-cyclohexyl-3-hydroxymethyloxetane was reacted with 4-(1,2-dibromoethyl)benzoyl chloride by the method of Procedure 2. The resulting product was characterized by NMR (300 MHz, $CDCl_3$): δ 1.0–1.4 and 1.6–2.0 (11H, m, cyclohexyl $CH_2$), 3.9–4.1 (2H, m, $CH_2Br$), 4.4 (2H, s, $CH_2O$), 4.55 (4H, d of d, $CH_2OCH_2$), 5.1 (1H, d of d, ArCHBr), 7.45 (2H, d, aromatic), 8.1 (2H, d, aromatic).

The oxetane ester produced by the above reaction was reacted with boron trifluoride etherate as described in Procedure 2 to yield 4-cyclohexyl-1-(4-(1,2-dibromoethyl)phenyl)-2,6,7-trioxabicyclo[2.2.2]octane. The product was characterized by NMR (300 MHz, $CDCl_3$): δ 0.9–1.3 and 1.5–1.9 (11H, m, cyclohexyl $CH_2$), 3.9–4.1 (2H, m, $CH_2Br$), 4.1 (6H, s, $(CH_2O)_3$), 5.1 (1H, d of d, ArCHBr), 7.35 (2H, d, aromatic), 7.6 (2H, d, aromatic).

The dibromoethylphenyl bicyclic was dehydrobrominated in accordance with the Procedure 2 to yield the desired 4-cyclohexyl-1-(4-ethynylphenyl)-2,6,7-trioxabicyclo[2.2.2]octane. The product was characterized by NMR (300 MHz, $CDCl_3$): δ 0.9–1.3 and 1.6–1.9 (11H, m, cyclohexyl $CH_2$), 3.05 (1H, s, C≡CH), 4.1 (6H, s, $(CH_2O)_3$), 7.45 (2H, d, aromatic), 7.55 (2H, d, aromatic). It was also characterized by mass spectometry ($[M+1]^+ = 299$) and was found to have a melting point of 190°–192° C.

Procedure 4

Preparation of 4-n-propyl-1-(4-ethynylphenyl)-2,6,7-trioxabicyclo[2.2.2.]octane

The compound 4-n-propyl-1-(4-ethynylphenyl)-2,6,7-trioxabicyclo[2.2.2]octane was synthesized utilizing the method set forth in Procedure 2. Reaction of the 3-n-propyl-3-hydroxymethyloxetane with 4-(1,2-dibromoethyl)benzoyl chloride led to the production of the corresponding oxetane ester which was characterized by NMR (300 MHz, $CDCl_3$): δ 0.95 (3H, t, $CH_3$), 1.35 (2H, m, $CH_3CH_2$), 1.75 (2H, m, $CH_3CH_2CH_2$), 3.95–4.1 (2H, m, $CH_2Br$), 4.45 (2H, s, $CH_2O$), 4.5–4.6 (4H, d of d, $CH_2OCH_2$), 5.1 (1H, d of d, ArCHBr), 7.5 (2H, d, aromatic), 8.05 (2H, d, aromatic). The oxetane ester was reacted with boron trifluoride etherate as described in Procedure 2 to provide 4-n-propyl-1-(4-(1,2-dibromoethyl)phenyl)-2,6,7-trioxabicyclo[2.2.2]octane. This compound was characterized by NMR (300 MHz, CDCl$_3$): δ 0.9 (3H, t, CH$_3$), 1.15–1.35 (4H, m, CH$_2$CH$_2$), 3.9–4.1 (2H, m, CH$_2$Br), 4.1 (6H, s, (CH$_2$O)$_3$), 5.1 (1H, d of d, ArCHBr), 7.35 (2H, d, aromatic), 7.6 (2H, d, aromatic).

The dibromo compound was dehydrobrominated to form the corresponding ethynyl compound, 4-n-propyl-1-(4-ethynylphenyl)-2,6,7-trioxabicyclo[2.2.2]octane by the method set forth in Procedure 2. The resulting product was characterized by NMR (300 MHz, CDCl$_3$): δ 0.9 (3H, t, CH$_3$), 1.15–1.35 (4H, m, CH$_2$CH$_2$), 3.05 (1H, s, C≡CH), 4.1 (6H, s, (CH$_2$O)$_3$), 7.45 (2H, d, aromatic), 7.55 (2H, d, aromatic). The compound was further characterized by mass spectometry ([M+1]$^+$=259) and was found to have a melting point of 127°–129° C.

Procedure 5

Biological Activity Determination LD$_{50}$ for *Musca domestica*

The compounds listed in Tables 1–5 were tested for insecticidal activity by dissolving them in acetone or in tetrahydrofuran if they were insoluble in acetone. Subsequent dilutions were prepared using the same solvent. The compound solutions (0.5 microliter) were applied topically to the ventrum of the abdomen of anesthetized adult female houseflies (*Musca domestica* L., SCR strain, 3-5 days after emergence, 20 mg each). The toxicity studies were varied by treating the houseflies topically with PB at 250 micrograms per gram, two to three hours prior to administering the toxicant. The treated houseflies were provided sugar and water, and mortality was determined after 24 hours at 25° C. The data in Tables 1–5 are reported at the lethal dose, in micrograms of toxicant per gram of insect weight required to kill 50% of the fly population and are referred to as the LD$_{50}$ values.

LD$_{50}$ for *Periplaneta americana*

The compounds listed in Table 6 were tested for toxicity to adult male American cockroaches (*Periplaneta americana*) by applying test solutions, as with *Musca domestica*, to the thorax using 1.0 microliter carrier solvent per insect. In each case the cockroaches were also tested after topical pretreatment with PB at 250 microgram/gram 2 hours before administering the trioxabicyclooctane. LD$_{50}$ values were established after 24 hours at 25° C. The compounds tested are strongly synergized by PB to achieve a potency similar to that with PB-treated houseflies except for two compounds (13 and 38) which are more than tenfold more toxic to houseflies than to cockroaches.

Other similar toxicity tests showed that compound 6 is also toxic to the mosquito larva, black bean aphid, German cockroach and milkweed bug. Thus, the wide range of usefulness of the new class of pesticides set forth herein has been established.

Industrial Applicability

The compounds of the present invention which have been synthesized have been found to have significant activity as pesticides. Furthermore, they are readily biodegradable.

We claim:

1. A compound comprising:

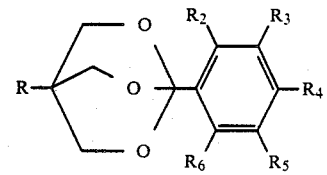

wherein R is C$_3$–C$_{10}$ normal- or branched-alkyl or cycloalkyl, C$_3$–C$_{10}$ normal- or branched-alkyl or cycloalkyl having one or more halogen, cyano, C$_1$–C$_2$ partially or completely halogenated alkyl, or C$_1$–C$_3$ alkoxy or partially or completely halogenated alkoxy substituents, C$_3$–C$_{10}$ cycloalkyl having C$_1$–C$_2$ alkyl substituents, phenyl, or phenyl having one or more halogen, cyano, nitro, ethynyl, C$_1$–C$_2$ alkyl or partially or completely halogenated alkyl, or C$_1$–C$_3$ alkoxy or partially or completely halogenated alkoxy substituent;

wherein at least one of R$_2$–R$_6$ is ethynyl; and wherein the remainder of R$_2$–R$_6$ are independently either hydrogen, halogen, C$_1$–C$_2$ alkyl, partially or completely halogenated, C$_1$–C$_2$ alkyl, C$_1$–C$_3$ alkoxy, partially or completely halogenated C$_1$–C$_3$ alkoxy, ethynyl, nitro, cyano, or azido.

2. A compound as set forth in claim 1, wherein R is normal or branched propyl or butyl, C$_3$–C$_{10}$ cycloalkyl or phenyl.

3. A compound as set forth in claim 1, wherein R is normal or branched propyl or butyl or cyclohexyl.

4. A compound as set forth in claim 1, wherein at least 1 of R$_3$, R$_4$ and R$_5$ is ethynyl and wherein the remainder of R$_2$–R$_6$ are independently hydrogen, fluorine, chlorine, bromine, cyano, CF$_3$, nitro, azido, ethynyl, methyl, ethyl, methoxy or ethoxy.

5. A compound as set forth in claim 4, wherein at least one of R$_3$, R$_4$ and R$_5$ is hydrogen.

6. A compound as set forth in claim 4, wherein at least two of R$_3$, R$_4$ and R$_5$ are hydrogen.

7. A compound as set forth in claim 1, wherein R$_3$ and R$_5$ are hydrogen and R$_4$ is ethynyl.

8. A pesticidal composition comprising an effective amount of a compound as set forth in claim 1, in combination with an inert carrier.

* * * * *